(12) United States Patent
Madabhushi et al.

(10) Patent No.: US 9,558,394 B2
(45) Date of Patent: Jan. 31, 2017

(54) HISTOGRAM OF HOSOYA INDEX (HOH) FEATURES FOR QUANTITATIVE HISTOMORPHOMETRY

(71) Applicant: Case Western Reserve University, Cleveland, OH (US)

(72) Inventors: Anant Madabhushi, Beachwood, OH (US); Ajay Basavanhally, Skillman, NJ (US); Sahirzeeshan Ali, Houston, TX (US)

(73) Assignee: Case Western Reserve University, Cleveland, OH (US)

( * ) Notice: Subject to any disclaimer, the term of this patent is extended or adjusted under 35 U.S.C. 154(b) by 187 days.

(21) Appl. No.: 14/600,094

(22) Filed: Jan. 20, 2015

(65) Prior Publication Data

US 2015/0254494 A1 Sep. 10, 2015

Related U.S. Application Data

(60) Provisional application No. 61/950,458, filed on Mar. 10, 2014.

(51) Int. Cl.
| | |
|---|---|
| *G06K 9/00* | (2006.01) |
| *G06T 7/00* | (2006.01) |
| *G06K 9/46* | (2006.01) |
| *G06F 19/00* | (2011.01) |

(52) U.S. Cl.
CPC ............ *G06K 9/0014* (2013.01); *G06F 19/345* (2013.01); *G06K 9/4642* (2013.01); *G06T 7/0012* (2013.01); *G06T 2207/10056* (2013.01); *G06T 2207/20072* (2013.01); *G06T 2207/20076* (2013.01); *G06T 2207/30024* (2013.01)

(58) Field of Classification Search
CPC ... G06F 19/345; G06K 9/0014; G06K 9/4642; G06T 2207/20072; G06T 2207/20076; G06T 2207/30024; G06T 7/0012
See application file for complete search history.

(56) References Cited

U.S. PATENT DOCUMENTS

| | | | | |
|---|---|---|---|---|
| 6,078,680 | A * | 6/2000 | Yoshida | G06T 7/0012 382/128 |
| 9,076,198 | B2 * | 7/2015 | Yoshihara | G06T 7/0081 |
| 2003/0103664 | A1 * | 6/2003 | Wei | G06T 7/0012 382/131 |
| 2004/0222379 | A1 * | 11/2004 | Cook | G01T 1/2985 250/363.03 |

(Continued)

*Primary Examiner* — Wesley Tucker
(74) *Attorney, Agent, or Firm* — Eschweiler & Associates, LLC

(57) ABSTRACT

Methods, apparatus, and other embodiments associated with classifying a region of cancerous tissue using a Histogram of Hosoya are described. One example apparatus includes a set of logics that acquires an image of a region of tissue demonstrating cancerous pathology, constructs a cell graph of the region of tissue, decomposes the cell graph into a set of subgraphs, computes a Hosoya Index for a subgraph, constructs a Histogram of Hosoya for the image based on the distribution of the subgraphs, and classifies the image based on the Histogram of Hosoya. Embodiments of example apparatus may generate and display the Histogram of Hosoya for the image. A prognosis for the patient may be provided based on the distribution of the histogram.

22 Claims, 8 Drawing Sheets

510  520  530

(56) References Cited

U.S. PATENT DOCUMENTS

| | | | | |
|---|---|---|---|---|
| 2004/0229816 A1* | 11/2004 | Paris | .................. | A61K 38/04 |
| | | | | 514/13.3 |
| 2006/0036372 A1* | 2/2006 | Yener | .................. | G06K 9/0014 |
| | | | | 702/19 |
| 2009/0129673 A1* | 5/2009 | Simon | .................. | G06T 7/0012 |
| | | | | 382/173 |
| 2009/0238457 A1* | 9/2009 | Rittscher | .............. | G06K 9/0014 |
| | | | | 382/171 |
| 2012/0106821 A1* | 5/2012 | Madabhushi | ......... | G06T 7/0012 |
| | | | | 382/133 |

\* cited by examiner 510    520    530

HISTOGRAM OF HOSOYA INDEX (HOH) FEATURES FOR QUANTITATIVE HISTOMORPHOMETRY

CROSS REFERENCE TO RELATED APPLICATIONS

This application claims the benefit of U.S. Provisional Application 61/950,458 filed Mar. 10, 2014.

BACKGROUND

Large complex networks frequently exhibit recurring subgraph patterns that can provide valuable insights into the organization of the underlying network structure. In histopathology, cell nuclei can be used for the construction of a cell graph (CG) that characterizes localized tissue architecture by constructing a series of disconnected subgraphs on an image. Conventional approaches to the quantification of subgraph similarity have traditionally relied on graph matching techniques that define graph matching and similarity as correspondence issues. However, the unstable and polynomial nature of conventional graph matching techniques makes them unsuitable for the analysis of large histopathology images that require computationally expensive explicit comparison of thousands of graphs. Conventional methods also fail to compare populations of subgraphs between various images that are decomposed via a CG into series of subgraphs.

Variations of tumor morphology relate to prognosis and patient outcomes. The primary means of diagnosing most cancers is histopathological examination of biopsy tissue to create a diagnostic profile based on cell morphology, cytoplasmic changes, cell density, and cell distribution. Visual characterization of tumor morphology via grading is, however, time consuming, highly subjective, and suffers from high inter-rater and intra-rater variability. Conventional visual grading of tumor morphology by a human pathologist may therefore be less than optimal in clinical situations where timely and accurate classification can affect patient outcomes.

Graph theory can be used to characterize the structure of large networks leading to improved understanding of dynamic interactions and patterns that exist between components of the network. Nodes with similar characteristics tend to cluster together forming sub-structures within the network. Sub-structures may be represented as subgraphs. Despite their complex nature, cancerous cells tend to self-organize in clusters and exhibit architectural organization.

Large networks often include subgraphs that provide valuable information on the interactions of nodes at a local level. Conventional methods that employ Voronoi (VT) graphs and Delaunay (DT) graphs may have biological context and potentially predict disease severity. However, conventional methods that employ VT graphs and DT graphs are limited to estimating global statistics. Conventional techniques and cell graphs may decompose an image into subgraphs by using clusters of nuclei as nodes, but do not identify similar subgraph structures that may recur across a population. Additionally, conventional approaches do not capture the effect of similar subgraph structures on overall tumor morphology.

BRIEF DESCRIPTION OF THE DRAWINGS

The accompanying drawings, which are incorporated in and constitute a part of the specification, illustrate various example apparatus, methods, and other example embodiments of various aspects of the invention. It will be appreciated that the illustrated element boundaries (e.g., boxes, groups of boxes, or other shapes) in the figures represent one example of the boundaries. One of ordinary skill in the art will appreciate that in some examples one element may be designed as multiple elements or that multiple elements may be designed as one element. In some examples, an element shown as an internal component of another element may be implemented as an external component and vice versa. Furthermore, elements may not be drawn to scale.

DETAILED DESCRIPTION

Figure 1:
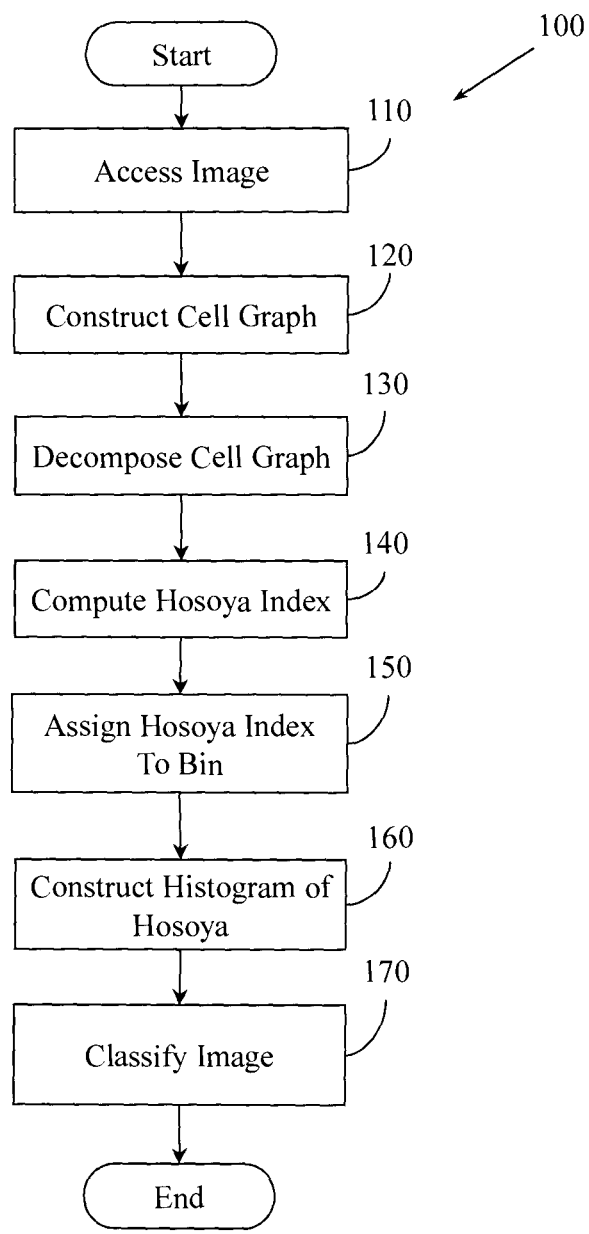
FIG. 1 illustrates an example method of classifying a region of cancerous tissue.

Variations in tumor morphology may be related to patient prognosis and outcome. Conventional methods of diagnosing cancer include visual histopathological examination of a biopsy to create a diagnostic profile based on variations in tumor morphology, including cell morphology, cytoplasmic changes, cell density, and cell distribution. Conventional methods of visually grading tumor morphology suffer from high subjectivity as well as intra and inter-reviewer variability. In contrast, example computerized quantified histomorphometric approaches characterize tumor morphology and predict patient outcomes in a more consistent and reproducible manner.

Some conventional automated tumor grading methods use graph theory to characterize the structure of large cellular networks. Nodes with similar characteristics tend to cluster together forming sub-graphs within the network. Cancerous cells tend to self-organize in clusters and may exhibit architectural organization. Subgraphs found within large networks may provide valuable information about local interactions between nodes. Conventional methods for predicting disease severity have employed VT and DT graphs built using nuclei as vertices. However, conventional methods using VT and DT are limited to analyzing global statistics, and fail to capture local features.

While other conventional approaches have employed CG to decompose an image into subgraphs using clusters of nuclei as nodes and encoding edge connections between only proximal nodes, these conventional approaches do not identify similar subgraph structures that recur across the population or their effect on overall tumor morphology. Conventional approaches employ graph matching and subgraph isomorphism algorithms to find similar graphs. However, graph matching and subgraph isomorphism algorithms are defined as node correspondence problems that are computationally expensive to solve. Conventional approaches are therefore sub-optimal when analyzing cancer tissue images that include hundreds or even thousands of subgraphs.

Example methods and apparatus predict patient outcomes more accurately than conventional methods by employing an image-based predictor to identify new features in breast, oropharyngeal, and oral cancers. Example methods and apparatus quantify tumor morphology by identifying populations of subgraphs that are similar within an image. Example methods and apparatus employ the Hosoya Index (HI) to identify groups of similar graphs in an image and to compare the image against other images of similar pathology. Example methods and apparatus define a range of HI values for a subgraph and construct a histogram of HI values for an image. Example methods and apparatus assign HI values to a plurality of discrete bins over an image. Example methods and apparatus define a signature based on the distribution of HI values.

Example methods and apparatus thus improve on conventional methods by constructing a histogram of Hosoya values across multiple subgraphs within an image. Example methods and apparatus distinguish low and high risk BCa patients on disease-free survival with an accuracy of at least 77%. Example methods and apparatus distinguish between p16+ OSCC progressors and p16+ OSCC non-progressors with an accuracy of at least 85%. Example methods and apparatus distinguish between oral cancer progressors and non-progressors with an accuracy of at least 80%. By increasing the accuracy with which different pathologies of cancer are distinguished, example methods and apparatus produce the concrete, real-world technical effect of increasing the probability that at-risk patients receive timely treatment tailored to the particular pathology they exhibit. The additional technical effect of reducing the expenditure of resources and time on patients who are less likely to suffer recurrence or disease progression is also achieved. Example methods and apparatus thus improve on conventional methods in a measurable, clinically significant way.

Some portions of the detailed descriptions that follow are presented in terms of algorithms and symbolic representations of operations on data bits within a memory. These algorithmic descriptions and representations are used by those skilled in the art to convey the substance of their work to others. An algorithm, here and generally, is conceived to be a sequence of operations that produce a result. The operations may include physical manipulations of physical quantities. Usually, though not necessarily, the physical quantities take the form of electrical or magnetic signals capable of being stored, transferred, combined, compared, and otherwise manipulated in a logic, and so on. The physical manipulations create a concrete, tangible, useful, real-world result.

It has proven convenient at times, principally for reasons of common usage, to refer to these signals as bits, values, elements, symbols, characters, terms, numbers, and so on. It should be borne in mind, however, that these and similar terms are to be associated with the appropriate physical quantities and are merely convenient labels applied to these quantities. Unless specifically stated otherwise, it is appreciated that throughout the description, terms including processing, computing, calculating, determining, and so on, refer to actions and processes of a computer system, logic, processor, or similar electronic device that manipulates and transforms data represented as physical (electronic) quantities.

Example methods may be better appreciated with reference to flow diagrams. While for purposes of simplicity of explanation, the illustrated methodologies are shown and described as a series of blocks, it is to be appreciated that the methodologies are not limited by the order of the blocks, as some blocks can occur in different orders and/or concurrently with other blocks from that shown and described. Moreover, less than all the illustrated blocks may be required to implement an example methodology. Blocks may be combined or separated into multiple components. Furthermore, additional and/or alternative methodologies can employ additional, not illustrated blocks.

FIG. 1 illustrates a computerized method 100 for classifying a region of cancerous tissue. Method 100 includes, at 110, accessing an image of a region of cancerous tissue. In one embodiment, accessing the image includes accessing a tissue microarray (TMA) core with a digital whole slide scanner. In different embodiments the image may be acquired from other sources that provide other fields of view, such as a whole slide digital image of a glass slide. The TMA core is digitized at 20× magnification and has a resolution of 0.33 μm per pixel. In other embodiments, other magnification levels and resolutions may be employed. In another embodiment, method 100 accesses a hematoxylin and eosin (H&E) stained TMA core at 400× magnification. The stained TMA core is a 0.6 mm TMA core or a 2 mm TMA core. In another embodiment, the H&E stained TMA core may be accessed at different magnification levels and have different dimensions.

Method 100 also includes, at 120, constructing a cell graph (CG) of the image. In one embodiment, a node of the CG represents a cluster of nuclei. Method 100, at 120, distinguishes nuclei within the image from the image background. In one embodiment, method 100 uses concavity detection to distinguish nuclei from the image background. In other embodiments, other techniques may be used to distinguish nuclei. The probability that a first node in the CG will be connected to a second node in the CG is based on a probabilistic decaying function of the Euclidean distance between the first node and the second node. For example, the cell graph CG may be defined as a graph G=(V, E), where V represents the set of nodes and E represents the edges of the graph. In this example, the probability that a link exists between a node u and a node v is based on the Euclidean distance between u and v.

Method 100 also includes, at 130, decomposing the CG into a set of disconnected subgraphs I, where I={$G_1$, $G_2$, . . . $G_m$}. The CG's topological space decomposes into its connected components. The connectedness relation between two pairs of points satisfies transitivity. Thus, if u~v and v~w, then u~w, which means that if there is a path from u to v and a path from v to w, the two paths may be concatenated together to form a path from u to w. The connected components of a graph G are therefore the largest induced subgraphs of G that are each connected.

Method 100 also includes, at 140, computing a Hosoya Index $Z(G_m)$ for a subgraph $G_m$, where $Z(G_m) \geq 0$. The Hosoya Index $Z(G_m)$ is defined as the number of subsets of a set of edges $E(G_m)$ in which no two edges in $G_m$ are adjacent. In graph theoretical terminology, the Hosoya Index $Z(G_m)$ is the total number of matchings of I, including the empty set. For example, for the cycle of four vertices $G_k=\{v_1, v_2, v_3, v_4\}$, all such subsets of $E(G_m)$ are $\emptyset, \{v_1, v_2\}$, $\{v_2,v_3\},\{v_3,v_4\},\{v_4,v_1\},\{v_1,v_2,v_3,v_4\},\{v_1,v_4,v_2,v_3\}$, so that the Hosoya Index $Z(G_m)=7$ in this example.

In one embodiment of method 100, the Hosoya Index is defined as $Z_0=\Sigma_{k=0}^{n}|a_k|=\Sigma_{k=0}^{n}b_k$. In this example, n is the number of vertices of the subgraph $G_m$. The kth coefficient of a matching polynomial is represented by $a_k$. The kth coefficient of a matching-generating polynomial is represented by $b_k$. The absolute value of $a_k$ is represented by $|a_k|$. In another embodiment, the Hosoya Index is defined as $Z_0=\Sigma_{k=0}^{\lfloor n/2 \rfloor}|a_k|$. In this embodiment, $\lfloor n/2 \rfloor$ denotes the floor function. In another embodiment, the ceiling function may be used instead of the floor function.

Method 100 also includes, at 150, assigning the Hosoya Index $Z(G_m)$ for a subgraph to a bin. Upon determining that $Z(G_m)$ is within a range, method 100 assigns $Z(G_m)$ to a bin associated with the range. In one embodiment, determining that $Z(G_m)$ is within a range includes determining if $Z(G_m)$ is within a first range, a second range, or a third range. For example, method 100, at 150, may assign $Z(G_m)$ to one of three discrete bins. If $Z(G_m)$ is within a first range of [0, 64], $Z(G_m)$ is assigned to a first bin associated with the first range. If $Z(G_m)$ is within a second range of [128, 1024], $Z(G_m)$ is assigned to a second bin associated with the second range. If $Z(G_m)$ is within a third range of [1025, ∞], $Z(G_m)$ is assigned to a third bin associated with the third range. In another embodiment, more than three ranges may be employed, and $Z(G_m)$ may be assigned to one of more than three discrete bins.

Method 100 also includes, at 160, constructing a histogram of $Z(G_m)$. The histogram of Hosoya indices represent the binned $Z(G_m)$ assigned at step 150. For example, when three discrete bins are employed, the histogram of $Z(G_m)$ displays three bars. In one embodiment, $Z(G_m)$ values of [0, 64] are defined as low. $Z(G_m)$ values of [128, 1024] are defined as intermediate, and $Z(G_m)$ values of [1025, ∞] are defined as high. By binning $Z(G_m)$ values as low, intermediate, and high, example methods and apparatus create a unique signature that represents populations of groups in the image accessed at 110. Example methods and apparatus facilitate comparing subgraph populations across a cohort of patients to look for recurring patterns indicative of disease outcome. Example methods and apparatus thus improve on conventional methods by predicting recurrence and classifying tumors as progressors or non-progressors with greater accuracy and in a more statistically intuitive way than conventional methods.

Method 100 also includes, at 170, controlling a computer aided diagnosis (CADx) system to classify the image based, at least in part, on the histogram. In one embodiment, a CADx system used for diagnosing BCa may be controlled by method 100 to classify TMA cores acquired from a patient demonstrating BCa pathology as likely to experience BCa recurrence or to not experience BCa recurrence. In another embodiment, method 100 may control a CADx system used for diagnosing OSCC p16+ or OCa cancer to classify a tumor as a progressor or a non-progressor.

Using a more appropriately determined and applied treatment may lead to less therapeutics being required for a patient or may lead to avoiding or delaying a biopsy, a resection, or other invasive procedure. When regions of cancerous tissue are more quickly and more accurately classified, patients with poorer prognoses may receive a higher proportion of scarce resources (e.g., therapeutics, physician time and attention, hospital beds) while those with better prognoses may be spared unnecessary treatment, which in turn spares unnecessary expenditures and resource consumption. Example methods and apparatus may thus have the real-world, quantifiable effect of improving patient outcomes.

While FIG. 1 illustrates various actions occurring in serial, it is to be appreciated that various actions illustrated in FIG. 1 could occur substantially in parallel. By way of illustration, a first process could construct a CG of an image, a second process could compute an HI for a subgraph of the CG, and a third process could construct a histogram of the HI. While three processes are described, it is to be appreciated that a greater or lesser number of processes could be employed and that lightweight processes, regular processes, threads, and other approaches could be employed.

Figure 2:
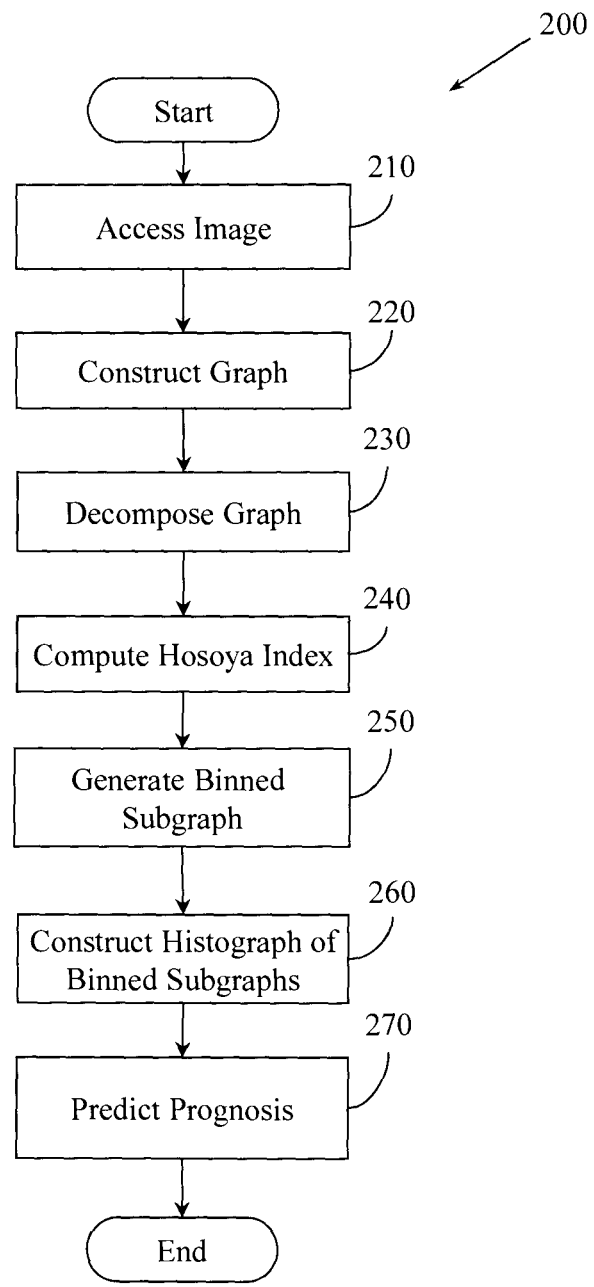
FIG. 2 illustrates an example method of predicting a prognosis from digital pathology images.

FIG. 2 illustrates an example method 200 for prognosis prediction from digital pathology images. Method 200 includes, at 210 accessing an image of a region of tissue from a patient demonstrating cancerous pathology. The image may be of a region of tissue demonstrating ER+ BCa pathology, p16+ OSCC pathology, or OCa pathology. In one embodiment, the image is accessed from a TMA core with a digital whole slide scanner. In other embodiments the image may be accessed from other sources including, for example, a whole slide digital image. The TMA core may be digitized at 20× magnification at a resolution of 0.33 µm per pixel. In another embodiment, method 200 accesses a 0.6 mm or 2 mm H&E stained TMA core at 400× magnification. In still other embodiments, the image may be of a region of tissue demonstrating other types of cancer, the TMA core may be accessed at different magnification levels or resolutions, or the TMA core may have different dimensions.

Method 200 also includes, at 220, constructing a graph of the image. In one embodiment, the graph may be a CG. Nodes of the graph represent cells or clusters of cells. Edges of the graph are defined by a probabilistic decaying function of the Euclidean distance between a first node and a second node. In one embodiment, cell nuclei are distinguished from the image background, and clusters of cells are identified for node assignment using concavity detection.

Method 200 also includes, at 230, decomposing the graph into a set of disconnected subgraphs. In one embodiment, the graph's topological space is decomposed into its connected components. The connectedness relation between two pairs of points within the graph satisfies transitivity.

Method 200 also includes, at 240, computing a Hosoya Index (HI) for a subgraph. The HI represents the number of subsets of the set of edges in the subgraph in which no two edges are adjacent. Method 200 also includes, at 250, generating a binned subgraph by assigning the subgraph to a bin based, at least in part, on the HI. The bins are discrete. In one embodiment, method 200 bins the HI values as low, intermediate, or high values. For example, HI values in the range [0, 64] may be binned as low, HI values in the range [128, 1024] may be binned as intermediate, and HI values greater than 1024 may be binned as high. In another embodiment, other ranges or numbers of ranges may be used.

Method 200 also includes, at 260, constructing a histogram of the binned subgraphs. In one embodiment, the histogram displays the distribution of HI values in the discrete bins.

Method 200 also includes, at 270, predicting a prognosis for the patient based on the distribution of the histogram. For example, a histogram that indicates that subgraphs with high HI values occur with greater frequency than subgraphs with low or intermediate HI values may indicate that the image from which the subgraph is constructed is more likely to be of a progressor than of a non-progressor. Method 200 may also, at 270, include controlling a CADx system to generate a prognosis prediction for the patient based on the distribution of the histogram. The CADx generated prognosis prediction may then be employed to complement a human pathologist's determination that the image represents a progressor or a non-progressor in a patient with OSCC or OCa cancer. In another embodiment, method 200 may generate prognosis predictions for patients demonstrating the pathology of other types of cancer, including prostate cancer.

In one example, a method may be implemented as computer executable instructions. Thus, in one example, a computer-readable storage medium may store computer executable instructions that if executed by a machine (e.g., computer) cause the machine to perform methods described or claimed herein including method 100 and method 200. While executable instructions associated with the listed methods are described as being stored on a computer-readable storage medium, it is to be appreciated that executable instructions associated with other example methods described or claimed herein may also be stored on a computer-readable storage medium. In different embodiments the example methods described herein may be triggered in different ways. In one embodiment, a method may be triggered manually by a user. In another example, a method may be triggered automatically.

Figure 3:
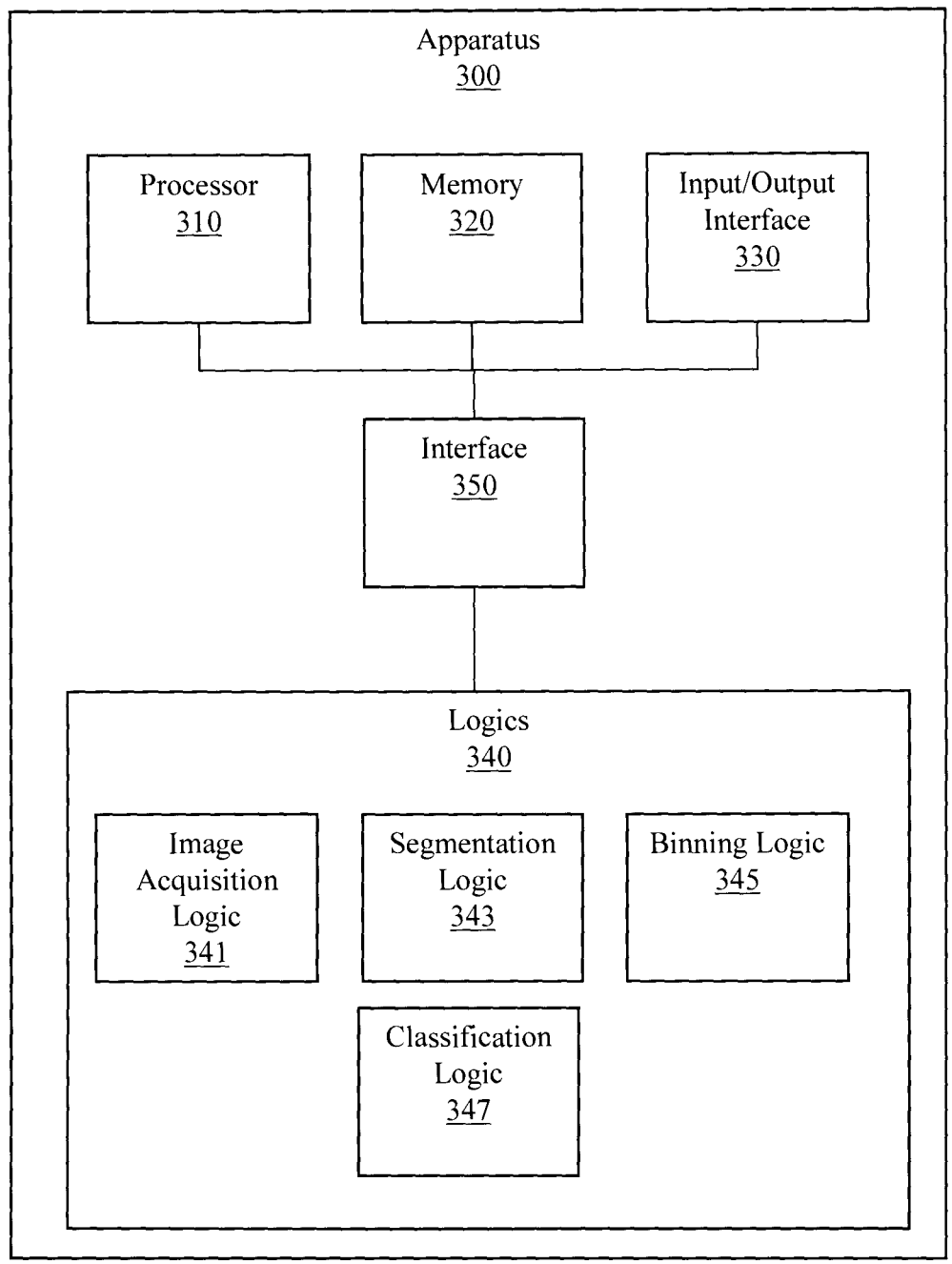
FIG. 3 illustrates an example apparatus that classifies a region of cancerous tissue in an image.

FIG. 3 illustrates an example apparatus 300 that classifies a region of cancerous tissue in an image. Apparatus 300 includes a processor 310, a memory 320, an input/output interface 330, a set of logics 340, and an interface 350 that connects the processor 310, the memory 320, the input/output interface 330, and the set of logics 340. The set of logics 340 includes an image acquisition logic 341, a segmentation logic 343, a binning logic 345, and a classification logic 347. In one embodiment, the functionality associated with the set of logics 340 may be performed, at least in part, by hardware logic components including, but not limited to, field-programmable gate arrays (FPGAs), application specific integrated circuits (ASICs), application specific standard products (ASSPs), system on a chip systems (SOCs), or complex programmable logic devices (CPLDs). In one embodiment, individual members of the set of logics 340 are implemented as ASICs or SOCs.

Image acquisition logic 341 acquires an image of a region of tissue. The region of tissue may be a section of tissue demonstrating cancerous pathology in a patient. In one embodiment, the image is of a TMA core digitized at 20× magnification with a 0.33 μm resolution per pixel. In another embodiment, the image is of an H&E stained TMA core at 400× magnification. The H&E stained TMA core may be a 0.6 mm TMA core, a 2 mm TMA core, or a TMA core with different dimensions. Other imaging approaches may be used to generate and access the image accessed by image acquisition logic 341.

Segmentation logic 343 constructs a graph of the image. In one embodiment the graph may be a CG. Segmentation logic 343 distinguishes cellular nuclei from a background of the image. In one embodiment, segmentation logic 343 uses concavity detection to assign a nuclei or a cluster of nuclei to a node. Segmentation logic 343 establishes an edge between a first node and a second, different node, using a probabilistic decaying function of the Euclidean distance between the first node and the second node. Segmentation logic 343 segments the graph into a set of disconnected subgraphs. The set of disconnected subgraphs are derived from a de-composition of the topological space of the graph. In another embodiment, segmentation logic 343 may distinguish cellular nuclei from the image background differently, and establish edges between nodes using a different function.

Binning logic 345 computes a Hosoya Index (HI) for a member of the set of disconnected subgraphs. Binning logic 345 computes the HI by calculating the number of adjacent subsets of the set of edges of a subgraph in which no two edges are adjacent. Binning logic 345 generates a histogram of the HI for members of the set of disconnected subgraphs. Binning logic 345 generates the histogram by assigning a subgraph to a discrete bin based on the HI. In one embodiment, the histogram includes at least three discrete bins. The three discrete bins may include a low HI range bin, an intermediate HI range bin, and a high HI range bin. In other embodiments, more than three discrete bins and more than three HI ranges may be employed.

Classification logic 347 classifies the image based on a distribution of the histogram. In one embodiment, classification logic 347 computes a probability of BCa recurrence in BCa tissue based on the distribution of the histogram. In another embodiment, classification logic 347 computes a probability that a p16+ OSCC tumor is a progressor, or that an OCa carcinoma tumor is a progressor. For example, classification logic 347 may determine that the distribution of the histogram for an image of a region of tissue demonstrating p16+ OSCC pathology indicates that subgraphs with high HI values occur with greater frequency than subgraphs with low HI values and subgraphs with intermediate HI values. Classification logic 347 then classifies the image as representing a p16+ OSCC progressor, based, at least in part, on the distribution of the histogram. In another embodiment, classification logic 347 may be employed to complement a human pathologist's determination that the image represents a progressor or a non-progressor in a patient with OSCC or OCa cancer. In another embodiment, apparatus 300 may classify regions of cancerous tissue in an image for a patient demonstrating the pathology of other types of cancer, including prostate cancer. In another embodiment, classification logic 347 may calculate the skewness of the histogram and classify the image based, at least in part, on the skewness. For example, a skewed-right histogram may indicate a lower chance of BCa recurrence, while a skewed-left histogram may indicate a higher chance of BCa recurrence. Classification logic 347 calculating the skewness of the histogram may enable a pathologist to correctly classify a section of tissue with more accuracy in situations where a visual inspection of the histogram may not indicate the skewness.

In another embodiment, classification logic 347 may control a computer aided diagnosis (CADx) system to classify the image based, at least in part, on the distribution of the histogram. For example, classification logic 347 may control a BCa CADx system to classify the image based, at least in part, on the distribution of the histogram. In other embodiments, other types of CADx systems may be controlled, including CADx systems for predicting patient prognosis among oral cancer, prostate cancer, colon cancer, lung cancer, bone metastases, and other diseases where disease classification and prognosis prediction may be based on cellular subgraph structural features captured and quantified in a histogram of Hosoya.

In one embodiment of apparatus 300, the set of logics 340 also includes a display logic. The display logic may control the CADx system to display the classification or histogram on a computer monitor, a smartphone display, a tablet display, or other displays. Displaying the classification or the histogram may also include printing the classification or the histogram. The display logic may also control the CADx to display an image of the region of tissue demonstrating cancerous pathology. The image of the region of tissue demonstrating cancerous pathology may include a histogram of Hosoya for the image. By displaying the histogram and the image of the region of cancerous tissue, example apparatus provide a timely and intuitive way for a human pathologist to more accurately classify pathologies demonstrated by a patient, thus improving on conventional approaches to predicting cancer recurrence and disease progression.

Figure 4:
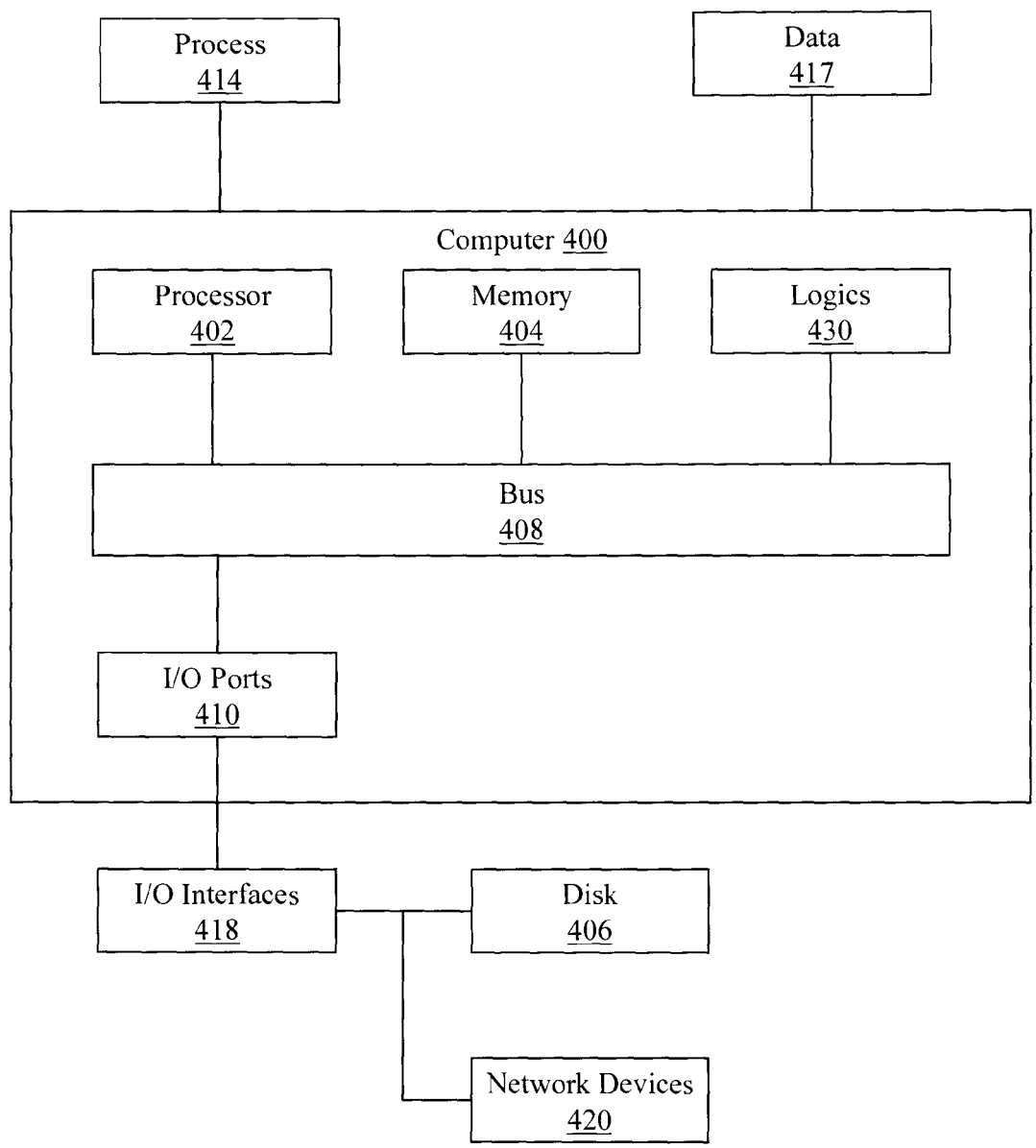
FIG. 4 illustrates an example computer in which example methods and apparatus described herein operate.

FIG. 4 illustrates an example computer 400 in which example methods illustrated herein can operate and in which example logics may be implemented. In different examples, computer 400 may be part of an MRI system, may be operably connectable to an MRI system, or may be part of a CADx system.

Computer 400 includes a processor 402, a memory 404, and input/output ports 410 operably connected by a bus 408. In one example, computer 400 may include a set of logics 430 that perform a method of classifying a region of cancerous tissue using a histogram of Hosoya. Thus, the set of logics 430, whether implemented in computer 400 as hardware, firmware, software, and/or a combination thereof may provide means (e.g., hardware, software) for classifying a region of cancerous tissue using a histogram of Hosoya. In different examples, the set of logics 430 may be permanently and/or removably attached to computer 400. In one embodiment, the functionality associated with the set of logics 430 may be performed, at least in part, by hardware logic components including, but not limited to, field-programmable gate arrays (FPGAs), application specific integrated circuits (ASICs), application specific standard products (ASSPs), system on a chip systems (SOCs), or complex programmable logic devices (CPLDs). In one embodiment, individual members of the set of logics 430 are implemented as ASICs or SOCs.

Processor 402 can be a variety of various processors including dual microprocessor and other multi-processor architectures. Memory 404 can include volatile memory and/or non-volatile memory. A disk 406 may be operably connected to computer 400 via, for example, an input/output interface (e.g., card, device) 418 and an input/output port 410. Disk 406 may include, but is not limited to, devices like a magnetic disk drive, a tape drive, a Zip drive, a flash memory card, or a memory stick. Furthermore, disk 406 may include optical drives like a CD-ROM or a digital video ROM drive (DVD ROM). Memory 404 can store processes 414 or data 417, for example. Disk 406 or memory 404 can store an operating system that controls and allocates resources of computer 400.

Bus 408 can be a single internal bus interconnect architecture or other bus or mesh architectures. While a single bus is illustrated, it is to be appreciated that computer 400 may communicate with various devices, logics, and peripherals using other busses that are not illustrated (e.g., PCIE, SATA, Infiniband, 1394, USB, Ethernet).

Computer 400 may interact with input/output devices via I/O interfaces 418 and input/output ports 410. Input/output devices can include, but are not limited to, digital whole slide scanners, an optical microscope, a keyboard, a microphone, a pointing and selection device, cameras, video cards, displays, disk 406, network devices 420, or other devices. Input/output ports 410 can include but are not limited to, serial ports, parallel ports, or USB ports.

Computer 400 may operate in a network environment and thus may be connected to network devices 420 via I/O interfaces 418 or I/O ports 410. Through the network devices 420, computer 400 may interact with a network. Through the network, computer 400 may be logically connected to remote computers. The networks with which computer 400 may interact include, but are not limited to, a local area network (LAN), a wide area network (WAN), or other networks.

Figure 5:
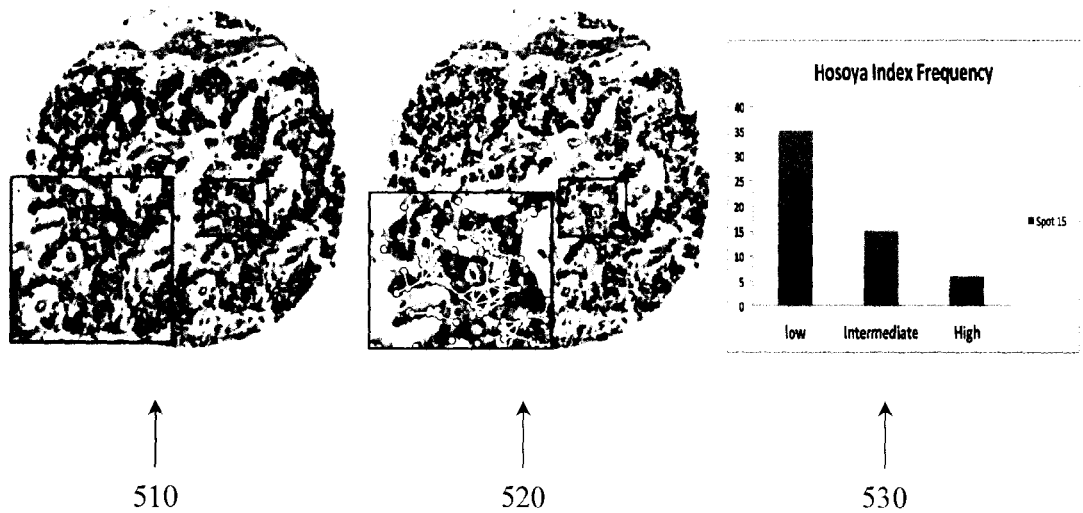
FIG. 5 illustrates a tissue microarray core (TMA) image of a section of tissue demonstrating breast cancer (BCa) pathology, and an associated histogram of Hosoya index frequency.

FIG. 5 illustrates a TMA image of a section of tissue demonstrating BCa pathology, and an associated histogram of Hosoya index frequency. Element 510 illustrates a section of BCa tissue that does not demonstrate BCa recurrence. Element 520 represents the same section of BCa tissue with a CG superimposed on the image. Element 530 is a histogram of the Hosoya index frequency for the graph illustrated in element 520. Histogram 530 may be generated by example methods and apparatus. The histogram 530 indicates that the TMA image is of a section of BCa tissue that does not demonstrate recurrence by the relatively higher frequency low range bin compared to the relatively lower frequency intermediate and high range bins. Histogram 530 is skewed to the right.

Figure 6:
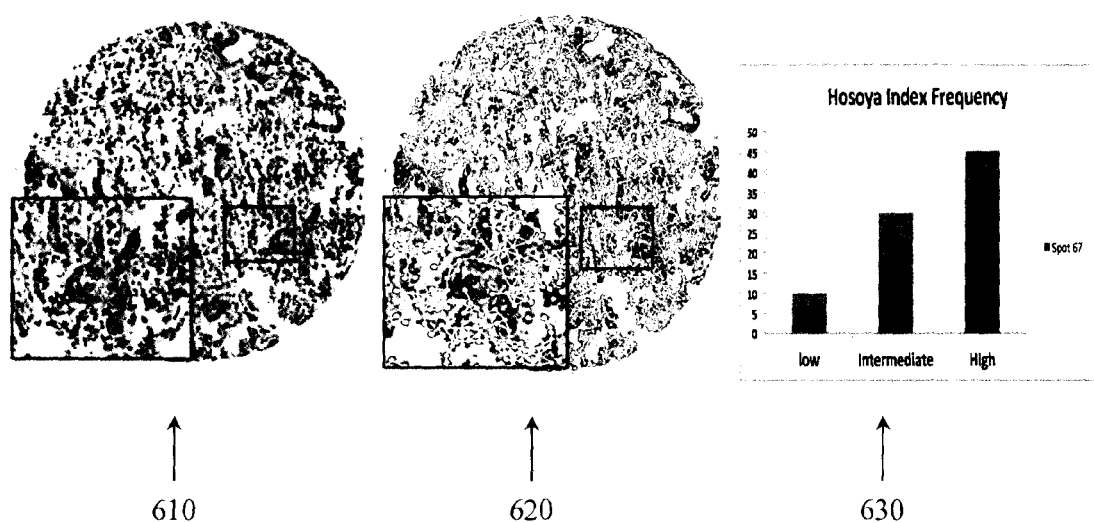
FIG. 6 illustrates a TMA image of a section of tissue demonstrating BCa pathology, and an associated histogram of Hosoya index frequency.

FIG. 6 illustrates a TMA image of a section of tissue demonstrating BCa pathology, and an associated histogram of Hosoya index frequency. Element 610 illustrates a section of BCa tissue that demonstrates BCa recurrence. Element 620 illustrates the same section of tissue as element 610, but with a CG superimposed. Element 630 is a histogram of the Hosoya index frequency for the CG illustrated in element 620. The histogram 630 indicates that the TMA image is of a section of BCa tissue that demonstrates recurrence by the relatively higher frequency high range bin compared to the relatively lower frequency intermediate and low range bins. Histogram 630 is skewed to the left.

Figure 7:
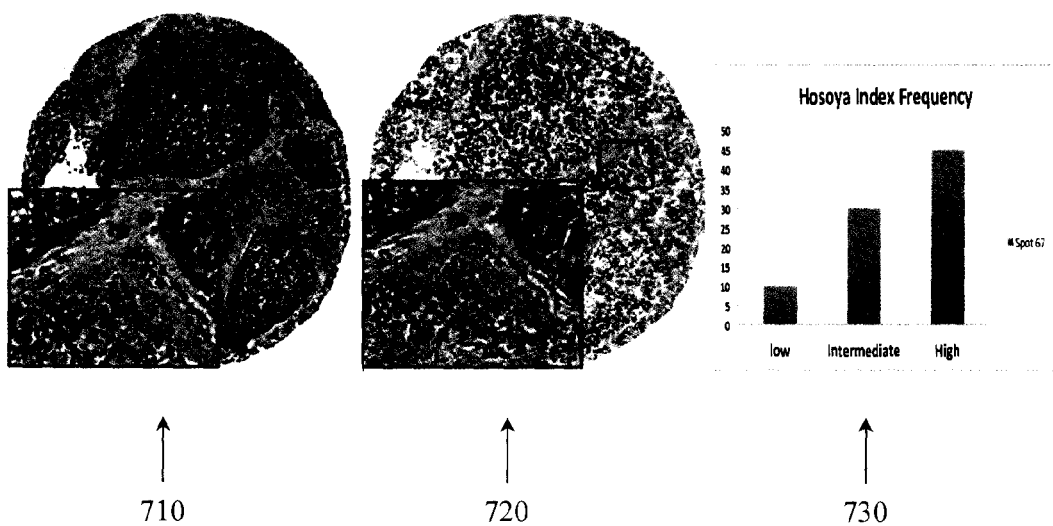
FIG. 7 illustrates a TMA image of a section of tissue demonstrating oral squamous cell carcinoma (OSCC) pathology, and an associated histogram of Hosoya index frequency.

FIG. 7 illustrates a TMA image of a section of tissue demonstrating OSCC pathology, and an associated histogram of Hosoya index frequency. Element 710 illustrates a section of a progressor OSCC tumor. Element 720 illustrates the same section of tissue as element 710, but with a CG superimposed. Element 730 is a histogram of the Hosoya index frequency for the CG illustrated in element 720. Histogram 730 is skewed to the left, indicating that the tumor illustrated in elements 710 and 720 is a progressor.

Figure 8:
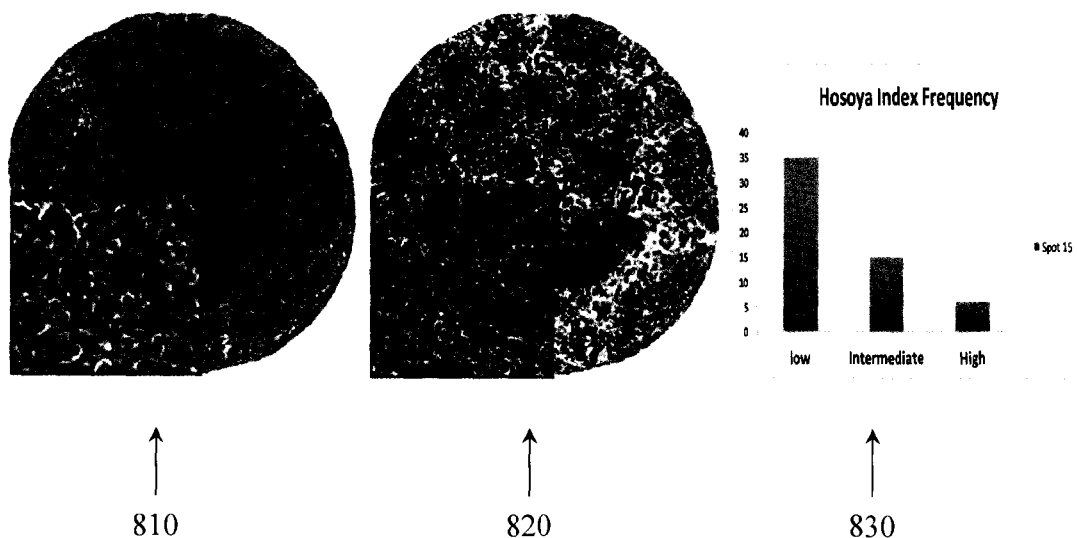
FIG. 8 illustrates a TMA image of a section of tissue demonstrating OSCC pathology, and an associated histogram of Hosoya index frequency.

FIG. 8 illustrates a TMA image of a section of tissue demonstrating OSCC pathology, and an associated histogram of Hosoya index frequency. Element 810 illustrates a section of a non-progressor OSCC tumor. Element 820 illustrates the same section of non-progressing tumor as element 810, but with a CG superimposed. Element 830 is a histogram of the Hosoya index frequency for the CG illustrated in element 820. Histogram 830 is skewed to the right, indicating that the tumor illustrated in elements 810 and 820 is a non-progressor. In other embodiments, graphical representations of the Hosoya index frequency for a TMA image other than a histogram may be employed.

References to "one embodiment", "an embodiment", "one example", and "an example" indicate that the embodiment(s) or example(s) so described may include a particular feature, structure, characteristic, property, element, or limitation, but that not every embodiment or example necessarily includes that particular feature, structure, characteristic, property, element or limitation. Furthermore, repeated use of the phrase "in one embodiment" does not necessarily refer to the same embodiment, though it may.

"Computer-readable storage medium", as used herein, refers to a medium that stores instructions or data. "Computer-readable storage medium" does not refer to propagated signals. A computer-readable storage medium may take forms, including, but not limited to, non-volatile media, and volatile media. Non-volatile media may include, for example, optical disks, magnetic disks, tapes, and other media. Volatile media may include, for example, semiconductor memories, dynamic memory, and other media. Common forms of a computer-readable storage medium may include, but are not limited to, a floppy disk, a flexible disk, a hard disk, a magnetic tape, other magnetic medium, an application specific integrated circuit (ASIC), a compact disk (CD), other optical medium, a random access memory (RAM), a read only memory (ROM), a memory chip or card, a memory stick, and other media from which a computer, a processor or other electronic device can read.

"Logic", as used herein, includes but is not limited to hardware, firmware, software in execution on a machine, or combinations of each to perform a function(s) or an action(s), or to cause a function or action from another logic, method, or system. Logic may include a software controlled microprocessor, a discrete logic (e.g., ASIC), an analog circuit, a digital circuit, a programmed logic device, a memory device containing instructions, and other physical devices. Logic may include one or more gates, combinations of gates, or other circuit components. Where multiple logical logics are described, it may be possible to incorporate the multiple logical logics into one physical logic. Similarly, where a single logical logic is described, it may be possible to distribute that single logical logic between multiple physical logics.

To the extent that the term "includes" or "including" is employed in the detailed description or the claims, it is intended to be inclusive in a manner similar to the term "comprising" as that term is interpreted when employed as a transitional word in a claim.

Throughout this specification and the claims that follow, unless the context requires otherwise, the words 'comprise' and 'include' and variations such as 'comprising' and Including' will be understood to be terms of inclusion and not exclusion. For example, when such terms are used to refer to a stated integer or group of integers, such terms do not imply the exclusion of any other integer or group of integers.

To the extent that the term "or" is employed in the detailed description or claims (e.g., A or B) it is intended to mean "A or B or both". When the applicants intend to indicate "only A or B but not both" then the term "only A or B but not both" will be employed. Thus, use of the term "or" herein is the inclusive, and not the exclusive use. See, Bryan A. Garner, A Dictionary of Modern Legal Usage 624 (2d. Ed. 1995).

While example systems, methods, and other embodiments have been illustrated by describing examples, and while the examples have been described in considerable detail, it is not the intention of the applicants to restrict or in any way limit the scope of the appended claims to such detail. It is, of course, not possible to describe every conceivable combination of components or methodologies for purposes of describing the systems, methods, and other embodiments described herein. Therefore, the invention is not limited to the specific details, the representative apparatus, and illustrative examples shown and described. Thus, this application is intended to embrace alterations, modifications, and variations that fall within the scope of the appended claims.

What is claimed is:

1. A non-transitory computer-readable storage medium storing computer executable instructions that when executed by a computer control the computer to perform a method for classifying a region of cancerous tissue, the method comprising:

accessing an image of a region of cancerous tissue;
constructing a cell graph (CG) of the image, where a node of the CG includes a cluster of nuclei, and where the probability that a first node in the CG will be connected to a second node in the CG is based on a probabilistic decaying function of the Euclidean distance between the first node and the second node;
decomposing the CG into a set of disconnected subgraphs I, where I={$G_1, G_2, \ldots G_m$};
computing a Hosoya Index $Z(G_m)$ for a subgraph $G_m$, where $Z(G_m) \geq 0$, and where $Z(G_m)$ is defined as the number of subsets of a set of edges $E(G_m)$ in which no two edges in $G_m$ are adjacent;
upon determining that $Z(G_m)$ is within a range, assigning $Z(G_m)$ to a bin associated with the range;
constructing a histogram of $Z(G_m)$; and
controlling a computer aided diagnosis (CADx) system to classify the image based, at least in part, on the histogram.

2. The non-transitory computer-readable storage medium of claim 1, where accessing an image of a region of cancerous tissue includes accessing a tissue microarray (TMA) core with a digital whole-slide scanner.

3. The non-transitory computer-readable storage medium of claim 2, where the TMA core is digitized at 20× magnification and 0.33 µm per pixel resolution.

4. The non-transitory computer-readable storage medium of claim 1, where accessing an image of a region of cancerous tissue includes accessing a hematoxylin and eosin (H&E) stained TMA core at 400× magnification, where the TMA core is a 0.6 mm TMA core or a 2 mm TMA core.

5. The non-transitory computer-readable storage medium of claim 1, where constructing the CG includes distinguishing nuclei within the image from the background of the image.

6. The non-transitory computer-readable storage medium of claim 5, the method including detecting the cluster of nuclei using concavity detection.

7. The non-transitory computer-readable storage medium of claim 6, where a cluster of nuclei includes overlapping cells, or cells that are within a threshold distance of each other.

8. The non-transitory computer-readable storage medium of claim 7, where the Hosoya Index $Z(G_m)$ is defined by $$Z_0 = \sum_{k=0}^{n} |a_k| = \sum_{k=0}^{n} b_k,$$

where n is the number of vertices of the subgraph $G_m$,
$a_k$ is the kth coefficient of a matching polynomial,
$b_k$ is the kth coefficient of a matching-generating polynomial, and
$|a_k|$ is the absolute value of $a_k$.

9. The non-transitory computer-readable storage medium of claim 8, where the Hosoya Index $Z(G_m)$ is defined by $Z_0 = \sum_{k=0}^{\lfloor n/2 \rfloor} |a_k|$, where $\lfloor n/2 \rfloor$ denotes the floor function.

10. The non-transitory computer-readable storage medium of claim 9, where determining that $Z(G_m)$ is within a range includes determining if $Z(G_m)$ is within a first range, a second range, or a third range.

11. The non-transitory computer-readable storage medium of claim 10, where the first range is [0, 64], the second range is [128, 1024], and the third range is [1025, ∞].

12. The non-transitory computer-readable storage medium of claim 11, where the image is of a region of ER+ breast cancer tissue, and where controlling the CADx system to classify the image based, at least in part, on the histogram, includes classifying the image as demonstrating early recurrence of ER+ breast cancer.

13. The non-transitory computer-readable storage medium of claim 11, where the image is of a region of a p16+ oral squamous cell carcinoma (OSCC) or oral cavity (OCa) cancer, and where controlling the CADx system to classify the image based, at least in part, on the histogram, includes classifying the image as a progressor or a non-progressor.

14. The non-transitory computer-readable storage medium of claim 10, where determining that $Z(G_m)$ is within a range includes determining if $Z(G_m)$ is within one of more than three ranges.

15. A non-transitory computer-readable storage medium storing computer executable instructions that when executed by a computer control the computer to perform a method for prognosis prediction from digital pathology images, comprising:
  accessing an image of a region of tissue from a patient demonstrating cancerous pathology;
  constructing a graph of the image, where nodes of the graph represent clusters of cells, and where edges of the graph are defined by a probabilistic decaying function of the distance between a first node and a second node;
  decomposing the graph into a set of disconnected subgraphs;
  computing a Hosoya Index (HI) for a subgraph;
  generating a binned subgraph by assigning the subgraph to a bin based, at least in part, on the HI;
  constructing a histogram of the binned subgraphs; and
  providing a prognosis for the patient based on the distribution of the histogram.

16. The non-transitory computer-readable storage medium of claim 15, where the graph is a cell graph.

17. An apparatus for classifying a region of cancerous tissue in an image, comprising:
  a processor;
  a memory;
  an input/output interface;
  a set of logics; and
  an interface to connect the processor, the memory, the input/output interface and the set of logics, where the set of logics includes:
    an image acquisition logic that acquires an image of a region of tissue demonstrating cancer pathology;
    a segmentation logic that constructs a graph of the image and segments the graph into a set of disconnected subgraphs;
    a binning logic that computes a Hosoya Index (HI) for a member of the set of disconnected subgraphs and generates a histogram of the HI for members of the set of disconnected subgraphs; and
    a classification logic that classifies the image based, at least in part, on a distribution of the histogram.

18. The apparatus of claim 17, where the segmentation logic distinguishes cellular nuclei from a background of the image, assigns a nuclei to a node based on concavity detection, and establishes an edge between a first node and a second node based on a probabilistic decaying function of the Euclidean distance between the first node and the second node.

19. The apparatus of claim 18, where the binning logic computes the HI by calculating the number of subsets of the set of edges of the subgraph in which no two edges are adjacent.

20. The apparatus of claim 19, where the binning logic generates the histogram of the HI for members of the set of disconnected subgraphs by assigning a subgraph to a discrete bin based on the HI, where the histogram includes at least three discrete bins.

21. The apparatus of claim 17, where the classification logic computes a probability of recurrence in breast cancer tissue, or computes a probability that a p16+ oropharyngeal squamous cell tumor or an oral cavity carcinoma tumor is a progressor.

22. The apparatus of claim 17, where the graph is a cell graph (CG).

* * * * *